(12) United States Patent
Hamilton et al.

(10) Patent No.: US 8,062,637 B2
(45) Date of Patent: Nov. 22, 2011

(54) METHODS OF AMELIORATING INFLAMMATORY DISEASE USING AN UPA ANTAGONIST

(75) Inventors: John Hamilton, Aberfeldie (AU); Ian Keith Campbell, Wantirna South (AU)

(73) Assignee: MorphoSys AG, Martinsried (DE)

( * ) Notice: Subject to any disclaimer, the term of this patent is extended or adjusted under 35 U.S.C. 154(b) by 33 days.

(21) Appl. No.: 12/499,817

(22) Filed: Jul. 9, 2009

(65) Prior Publication Data
US 2009/0274702 A1 Nov. 5, 2009

Related U.S. Application Data

(63) Continuation-in-part of application No. 11/856,949, filed on Sep. 18, 2007, which is a continuation of application No. 09/851,230, filed on May 8, 2001, now Pat. No. 7,455,836.

(60) Provisional application No. 60/202,392, filed on May 8, 2000.

(51) Int. Cl.
*A61K 39/40* (2006.01)
*A61K 39/00* (2006.01)
(52) U.S. Cl. .................. 424/139.1; 424/184.1
(58) Field of Classification Search .............. None
See application file for complete search history.

(56) References Cited

U.S. PATENT DOCUMENTS

| | | | |
|---|---|---|---|
| 5,444,153 A | 8/1995 | Goss et al. | |
| 5,475,087 A | 12/1995 | Seelig et al. | |
| 5,662,609 A | 9/1997 | Slepian | |
| 5,747,032 A | 5/1998 | Metcalf et al. | |
| 5,837,460 A | 11/1998 | von Feldt et al. | |
| 5,962,477 A | 10/1999 | Mak | |
| 6,200,567 B1 | 3/2001 | Lopez et al. | |
| 6,482,403 B1 | 11/2002 | Sim et al. | |
| 6,833,357 B2 * | 12/2004 | Cines et al. .................. | 514/12.1 |
| 2002/0141004 A1 * | 10/2002 | Hayashi ........................ | 358/519 |
| 2009/0041755 A1 * | 2/2009 | Eriksson ..................... | 424/130.1 |
| 2009/0232799 A1 * | 9/2009 | Abraham .................... | 424/133.1 |

FOREIGN PATENT DOCUMENTS

| | | |
|---|---|---|
| JP | 11244595 | 9/1999 |
| JP | 2000-198799 | 7/2000 |
| WO | 9728190 | 8/1997 |
| WO | 0009561 | 2/2000 |

OTHER PUBLICATIONS

Williamson, D.J. et al., The detection and initial characterization of colony-stimulating factors in synovial fluid, Clinical & Experimental Immunology 72:67-73, 1988.
Xu, W.D. et al., Cytokines in chronic inflammatory arthritis. II Granulocyte-macrophage colony-stimulating factor in rheumatoid synovial effusions. J Clin Invest 83:876-882, 1989.
Leizer, T. et al. Cytokine regulation of colony-stimulating factor production in cultured human synovial fibroblasts: I. Induction of GM-CSF and G-CSF production by interleukin-1 and tumor necrosis factor. Blood 76:1989-1996, 1990.
Alvaro-Gracia J. et al., Cytokines in chronic inflammatory arthritis. VI. Analysis of the synovial cells involved in granulocyte-macrophage colony-stimulating factor production and gene expression in rheumatoid arthritis and its regulation by IL-1 and tumor necrosis factor-alpha. J Immunol 146:3365-3371, 1991.
De Vries, G. et al., Flare-up of rheumatoid arthritis during GM-CSF treatment after chemotherapy. Lancet 338:517-518, 1991.
Hazenberg, B. et al., Correction of granulocytopenia in Felty's syndrome by granulocyte-macrophage colony-stimulating factor. Simultaneous induction of interleukin-6 release and flare-up of the arthritis. Blood 74:2769-2770, 1989.
Lubbe, A.S. et al., Improvement of pneumonia and arthritis in Felty's syndrome by treatment with granulocyte-macrophage colony-stimulating factor (GM-CSF). Blut 61:379-380, 1990.
Kaiser, U. et al., Felty's syndrome: favorable response to granulocyte-macrophage colony-stimulating factor in the acute phase. Acta Haematol 87:190-194, 1992.
Krishnaswamy, G. et al., Resolution of the neutropenia of Felty's syndrome by longterm administration of recombinant granulocyte colony stimulating factor. J Rheumatol 23:763-765, 1996.
Campbell, I.K. et al., Granulocyte-macrophage colony stimulating factor exacerbates collagen induced arthritis in mice. Ann Rheum Dis 56:364-368, 1997.
Metcalf, D., The Florey Lecture, 1991. The colony-stimulating factors: discovery to clinical use. Philos Trans R Soc Lond B Biol Sci 333:147-173, 1991.
Robertson, F.M. et al., Granulocyte-macrophage colony stimulating factor gene expression and function during tumor promotion. Carcinogenesis 15:1017-1029, 1994.
Vasunia, K.B. et al., Granulocyte-macrophage colony-stimulating factor (GM-CSF) is expressed in mouse skin in response to tumor-promoting agents and modulates dermal inflammation and epidermal dark cell numbers. Carcinogenesis 15:653-660, 1994.
Hercus, T. et al., Specific Human Granulocyte-Macrophage Colony-Stimulating Factor Antagonists. PNAS 91:5838-5842, 1994.
Kinne, R.W. et al., Macrophages in rheumatoid arthritis. Arthritis Res 2:189-202, 2000.
Stanley, E. et al., Granulocyte/macrophage colony-stimulating factor-deficient mice show no major perturbation of hematopoiesis but develop a characteristic pulmonary pathology. Proc Natl Acad Sci U S A 91:5592-5596, 1994.
Paine, R. et al., Impaired functional activity of alveolar macrophages from GM-CSF-deficient mice. Am J Physiol Lung Cell Mol Physiol 281:L1210-1218, 2001.
Dranoff, G. et al., Involvement of granulocyte-macrophage colony-stimulating factor in pulmonary homeostasis. Science 264:713-716, 1994.

(Continued)

*Primary Examiner* — Michail Belyavskyi (57) ABSTRACT

The present invention relates generally to a method for the treatment and prophylaxis of inflammatory conditions. The present invention is predicated in part on the identification of cells of the monocyte/macrophage lineage being critical for inflammation and, in particular, chronic inflammation. In accordance with the present invention, it is proposed that the reduction in levels of monocyte/macrophage-type cells and/or a reduction in the production of inflammatory and pro-inflammatory mediators by these cells, especially locally, is effective in reducing inflammatory conditions. The present invention further provides animal models useful for screening for reducing levels of monocyte/macrophage-type cells and/or reducing the production of inflammatory and pro-inflammatory mediators of these cells.

7 Claims, 7 Drawing Sheets

OTHER PUBLICATIONS

Coyle, A.J. et al., Interleukin-4 is required for the induction of lung Th2 mucosal immunity. Am J Respir Cell Mol Biol 13:54-59, 1995.
Finkelman, F.D. et al., Anti-cytokine antibodies as carrier proteins. Prolongation of in vivo effects of exogenous cytokines by injection of cytokine-anti-cytokine antibody complexes. J Immunol 151:1235-1244, 1993.
Sato, T.A. et al., Recombinant soluble murine IL-4 receptor can inhibit or enhance IgE responses in vivo. J Immunol 150:2717-2723, 1993.
Else, K.J. et al., Cytokine-mediated regulation of chronic intestinal helminth infection. J Exp Med 179:347-351, 1994.
Beavitt, S.-J.E. et al., Lyn-Deficient Mice Develop Severe, Persistent Asthma: Lyn Is a Critical Negative Regulator of Th2 Immunity, The Journal of Immunology, 2005, 175: 1867-1875.
Campbell, I.K. et al., Protection from Collagen-Induced Arthritis in Granulocyte-Macrophage Colony-Stimulating Factor-Deficient Mice, The Journal of Immunology, 1998, 161:3639-3644.
Campbell, I.K. et al., The colony-stimulating factors and collagen-induced arthritis: exacerbation of disease by M-CSF and G-CSF and requirement for endogenous M-CSF, Journal of Leukocyte Biology, vol. 68, Jul. 2000, 144-150.
Campbell, I.K. et al., Humanarticular Caritilage and Chondrocytes Produce Hemopoietic Colony-Stimulating Factors in Culture in Response to IL-1, The Journal of Immunology Vo. 147. 1238-1246, No. 4, Aug. 15, 1991.
Firestein, G.S. et al., Cytokines in Chronic Inflammatory Arthritis, The Rockefeller University Press vol. 168, Nov. 1988, 1573-1586.
Nakajima, H. et al., The effect of treatment with interferon-gamma on type II collagen-induced arthritis, Clin. exp. Immunol. 81, 441-445, 1990.
Joosten, L.A.B. et al., Dual Role of IL-12 in Early and Late Stages of Murine Collagen Type II Arthritis, The Journal of Immunology, 1997, 159: 4094-4102.
Szeliga, J. et al., IL-12 promotes cellular but not humoral type II collagen-specific Th1-type responses in C57BL/6 and B10. Q mice and fails to induce arthritis, International Immunology, vol. 8, No. 8, 1221-1227, 1996.
Campbell, I.K. et al., Production of macrophage colony-stimulating factor (M-CSF) by human articular cartilage and chondrocytes. Mudulation by interleukin-1 and tumor necrosis factor α, Biochimica et Biophysica Acra, 1182 57-63, 1993.
Campbell, I.K. et al., Collagen-induced arthritis in C57BL/6(H-2b) mice: new insights into an important disease model of rheumatoid arthritis, Eur. J. Immunol. 2000, 30: 1568-1575.
Hamilton, J.A. et al., Regulation of Macrophage Colony-Stimulating Factor (M-CSF) Production in Cultured Human Synovial Fibroblasts, Growth Factors, 1993, vol. 9, 157-165.
Mauritz, N.J. et al., Treatment With Gamma-Interferon Triggers the Onset of Collagen Arthritis in Mice, Arthritis and Rheumatism, vol. 31, No. 10, 1988.
Germann, T. et al., Characterization of the Adjuvant Effect of IL-12 and Efficacy of IL-12 Inhibitors in Type II Collagen-Induced Arthritis, Annal. NY Acad. Sci., Oct. 31, 1996, 795: 227-240.
McIntyre, K.W. et al., Reduced incidence and severity of collagen-induced arthritis in interleukin-12-deficient mice, Eur. J. Immunol. 1996, 26: 2933-2938.
Boissier, M.-C. et al., Biphasic effect of interferon-y in murine collagen-induced arthritis, Eur. J. Immunol. 1995, 25: 1184-1190.

Nagata M, Yamamoto H, Tabe K, Sakamoto Y, Matuo H: Eosinophil-Adhension-Inducing Activity Produced by Antigen-Stimulated Mononuclear Cells Involves GM-CSF. Int Arch Allergy Immunol 2000; 122(Suppl. 1):15-19 (DOI: 10.1159/000053625).
Yuan H. Yang and John A. Hamilton: Dependence of Interleukin-1-Induced Arthritis on Granulocyte-Macrophage Colony-Stimulating Factor Arthritis & Rheumatism vol. 44, No. 1, Jan. 2001, pp. 111-119.
Belcher C, Fawthrop F, Bunning R, Doherty M. Plasminogen activators and their inhibitors in synovial fluids from normal, osteoarthritis, and rheumatoid arthritis knees. Ann Rheum Dis 1996;55:230-6.
Brommer EJ, Dooijewaard G, Dijkmans BA, Breedveld FC. Plasminogen activators in synovial fluid and plasma from patients with arthritis. Ann Rheum Dis 1992;51:965-8.
Busso N, Peclat V, So A, Sappino AP. Plasminogen activation in synovial tissues: differences between normal, osteoarthritis, and rheumatoid arthritis joints. Ann Rheum Dis 1997;56:550-7.
Busso N, Peclat V, Van Ness K, Kolodziesczyk E, Degen J, Bugge T, et al. Exacerbation of antigen-induced arthritis in urokinase-deficient mice. J Clin Invest 1998;102(1):41-50.
Cerinic MM, Generini S, Partsch G, Pignone A, Dini G, Konttinen YT, et al. Synoviocytes from osteoarthritis and rheumatoid arthritis produce plasminogen activators and plasminogen acti-Coagulation and the PA/Plasmin System in RA 2277 vator inhibitor-1 and display u-PA receptors on their surface. Life Sci 1998;63:441-53.
Ganu VS, Goldberg RL, Blancuzzi VJ, Wilson DE, Doughty J, Melton R, et al. Elevation of synovial plasminogen activator activity after injection of interleukin-1 alpha into rabbit knee joint. Agents Actions 1991;34:226-8.
Hamilton JA, Campbell IK, Wojta J, Cheung D. Plasminogen activators and their inhibitors in arthritic disease. Ann N Y Acad Sci 1992;667:87-100.
Hamilton JA, Slywka J. Stimulation of human synovial fibroblast plasminogen activator production by mononuclear cell supernatants. J Immunol 1981;126:851-5.
Kitching AR, Holdsworth SR, Ploplis VA, Plow EF, Collen D, Carmeliet P, et al. Plasminogen and plasminogen activators protect against renal injury in crescentic glomerulonephritis. J Exp Med 1997;185:963-8.
Nielsen BS, Sehested M, Duun S, et al. Urokinase plasminogen activator is localized in stromal cells in ductal breast cancer. Lab Invest. 2001;81:1485-1501.
Petersen HH, Hansen M, Schousboe SL, Andreasen PA. Localization of epitopes for monoclonal antibodies to urokinase-type plasminogen activator: relationship between epitope localization and effects of antibodies on molecular interactions of the enzyme. Eur J Biochem. 2001;268:4430-4439.
Ronday HK, Smits HH, van Muijen GN, Pruszczynski MS, Dolhain RJ, van Langelaan EJ, et al. Difference in expression of the plasminogen activation system in synovial tissue of patients with rheumatoid arthritis and osteoarthritis. Br J Rheumatol 1996;35:416-23.
Van Der Laan WH, Pap T, Ronday HK, Grimbergen JM, Huisman LGM, TeKoppele JM, et al. Cartilage degradation and invasion by rheumatoid synovial fibroblasts is inhibited by gene transfer of a cell surface-targeted plasmin inhibitor. Arthritis Rheum 2000;43:1710-8.
Yang YH, Carmeliet P, Hamilton JA. Tissue-type plasminogen activator deficiency exacerbates arthritis. J Immunol 2001;167: 1047-52.

\* cited by examiner

METHODS OF AMELIORATING INFLAMMATORY DISEASE USING AN UPA ANTAGONIST

This application is a continuation-in-part of application Ser. No. 11/856,949, filed Sep. 18, 2007, now pending, which is a continuation of application Ser. No. 09/851,230, filed May 8, 2001, now patented, which is a non-provisional of application Ser. No. 60/202,392, filed May 8, 2000, which applications are incorporated-by-reference in their entireties.

FIELD OF THE INVENTION

The present invention relates generally to a method for the treatment and prophylaxis of inflammatory conditions. The present invention is predicated in part on the identification of cells of the monocyte/macrophage lineage being critical for inflammation and, in particular, chronic inflammation. In accordance with the present invention, it is proposed that the reduction in levels of monocyte/macrophage-type cells and/or a reduction in the production of inflammatory and pro-inflammatory mediators by these cells, especially locally, is effective in reducing inflammatory conditions. The present invention further provides animal models useful for screening for reducing levels of monocyte/macrophage-type cells and/or reducing the production of inflammatory and pro-inflammatory mediators of these cells. Antagonists of the invention may be used in combination with any other conventionally available therapeutic agent.

BACKGROUND OF THE INVENTION

Cytokines impart signals to cells to regulate the immune response, control cell proliferation and differentiation and to regulate the operation of the cytokine network. However, the pleiotropic nature of cytokines is such that in addition to their beneficial effects, cytokines can also induce adverse side effects such as alteration of normal cell growth, undesirable modulation of the functional activity of other cytokines or other unwanted immune effects such as severe inflammation, fever, malaise, nausea or modulation of haemopoiesis.

Inflammation is a particularly important physiological process with effects ranging from minor discomfort to life threatening situations. Macrophages are the key cells in chronic inflammatory lesions which produce a range of inflammatory and pro-inflammatory mediators such as Tumour Necrosis Factor .alpha. (TNF-.alpha.) and Interleukin-1 (IL-1). TNF-.alpha. and IL-1 are proposed to be associated with rheumatoid arthritis, inflammatory bowel disease, Crohns disease, type I diabetes, multiple sclerosis, psoriasis and chronic obstructive lung disease, such as asthma, chronic bronchitis, emphysema and chronic obstructive airway disease. It has been previously proposed to use anti-inflammatory glucocorticoids, which act, at least in part, to suppress macrophage production of TNF-.alpha., IL-1 and other pro-inflammatory mediators. However, although effective, the use of anti-inflammatory glucocorticoids poses therapeutic difficulties given that their receptors are widespread in the body.

In work leading up to the present invention, the inventors proposed to adopt a strategy of lowering monocyte/macrophage levels and/or reducing their level of activation, especially at a site of inflammation in the treatment of inflammatory conditions. The method developed by the instant inventors does not require knowledge of which pro-inflammatory mediator(s) is (are) more relevant to a particular inflammatory condition than another pro-inflammatory mediator.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention contemplates a method for ameliorating the effects of inflammation in a subject, said method comprising administering an agent which inhibits or otherwise antagonizes the effects of a colony stimulating factor on cells of the monocyte/macrophage lineage thereby reducing the level of proliferation, activation, growth and/or survival of said cells.

In a particularly preferred aspect, the present invention provides a method for ameliorating the effects of inflammation in a subject, said method comprising administering an agent which inhibits or otherwise antagonizes the effects of two or more colony stimulating factors on cells of the monocyte/macrophage lineage thereby reducing the level of proliferation, activation, growth and/or survival of said cells.

Another aspect of the present invention contemplates a method for ameliorating the effects of inflammation in a subject, said method comprising administering an agent which inhibits or otherwise antagonizes the effects on M-CSF and/or GM-CSF on cells of the monocyte/macrophage lineage thereby reducing the level of proliferation, activation, growth and/or survival of said cells.

Yet another aspect of the present invention provides a method for ameliorating the effects of inflammation in a subject, said method comprising administering an agent which inhibits or otherwise antagonizes the activity of u-PA and optionally other inflammatory mediators produced by a cell of the monocyte/macrophage lineage.

Still yet another aspect of the present invention provides a method for ameliorating the effects of inflammation in a subject, said method comprising administering one or more agents to antagonize the effects of a colony-stimulating factor on cells of the monocyte/macrophage lineage thereby reducing cell proliferation, activation, growth and/or survival and which antagonize the effects of u-PA and optionally other inflammatory mediators produced by said cells of monocyte/macrophage lineage.

Even still another aspect of the present invention is directed to a composition comprising one or more molecules capable of antagonizing the ability of a colony-stimulating factor from activating, proliferating, inducing growth and/or survival of cells of a monocyte/macrophage lineage, said composition further comprising one or more pharmaceutically acceptable carriers and/or diluents.

More particularly, the present invention provides a composition comprising one or more agents capable of antagonizing the effects of two or more colony-stimulating factors on cells of the macrophage lineage thereby reducing cell proliferation and/or activation and optionally an agent which antagonizes the effects of u-PA produced by said cells of macrophage lineage.

Even still yet another aspect of the present invention provides a composition comprising two immunointeractive molecules wherein one is specific for M-CSF and another is specific for GM-CSF, said composition further comprising one or more pharmaceutically acceptable carriers and/or diluents wherein said composition is useful in the treatment of inflammation.

Another aspect of the present invention is directed to a composition comprising an antagonist of u-PA and optionally an antagonist of one or more other inflammatory mediators produced by cells from monocyte/macrophage lineage and one or more pharmaceutically acceptable carriers and/or diluents.

Yet another embodiment of the present invention provides a composition comprising immunointeractive molecules to M-CSF and GM-CSF and an antagonist of u-PA and optionally one or more antagonists to one or more other inflammatory mediators produced by cells of a monocyte/macrophage lineage and one or more pharmaceutically acceptable carriers and/or diluents.

Still yet another embodiment of the present invention contemplates a method for ameliorating the effects of inflammation in a subject, said method comprising administering to said subject an effective amount of an agent comprising a monocyte/macrophage interacting ligand chemically linked to an active portion and wherein said agent is in an encapsulated form such that the monocyte/macrophage interacting portion is represented on the outer surface of said encapsulation while the active portion is part of the encapsulated wall or is internal relative to the encapsulation wall such that a monocyte/macrophage cell is capable of internalizing said encapsulated agent and wherein said active portion of said agent antagonizes colony-stimulating factor mediated proliferation, activation, growth and/or survival of said monocyte/macrophage cell and/or antagonizes the production or activity of one or more inflammatory mediators from said monocyte/macrophage cells.

Even yet another embodiment of the present invention is directed to a method for ameliorating the effects of inflammation in a subject, said method comprising administering to said subject an effective amount of an agent comprising a monocyte/macrophage interacting ligand chemically linked to an active portion or a pro-active form thereof and wherein said active portion of said agent antagonizes colony-stimulating factor mediated proliferation, activation, growth and/or survival of said monocyte/macrophage cell and/or antagonizes the production or activity of one or more inflammatory mediators from said monocyte/macrophage cells.

Another aspect of the present invention is directed to an agent comprising a monocyte/macrophage interacting ligand chemically linked to an active portion and wherein said agent is in an encapsulated form such that the monocyte/macrophage interacting portion is represented on the outer surface of said encapsulation while the active portion is part of the encapsulated wall or is internal relative to the encapsulation wall such that a monocyte/macrophage cell is capable of internalizing said encapsulated agent and wherein said active portion of said agent antagonizes colony-stimulating factor mediation, proliferation, activation, growth and/or survival of said monocyte/macrophage and/or antagonizes the production or activity of one or more inflammatory mediators.

Yet another aspect of the present invention comprises administering to said subject an effective amount of an agent comprising a monocyte/macrophage interacting ligand chemically linked to an active portion or a pro-active form thereof and wherein said active portion of said agent antagonizes colony-stimulating factor mediated proliferation, activation, growth and/or survival of said monocyte/macrophage cell and/or antagonizes the production or activity of one or more inflammatory mediators from said monocyte/macrophage cells.

BRIEF DESCRIPTION OF THE DRAWINGS

FIG. 1 is a diagrammatic representation highlighting the therapeutic concept behind the present invention. In essence, macrophages are the critical targets in chronic inflammation. Colony-stimulating factors such as M-CSF and GM-CSF stimulate survival, proliferation and activation of macrophages resulting in production of pro-inflammatory mediators such as IL-1, TNF-.alpha. and/or u-PA.

FIG. 2B is a graphical representation showing the effect of anti-GM-CSF antibody on CIA development. DBA/1 mice were given a boost of collagen type II at day 21. At day 27, CIA positive mice (n=10/group) were given 300 .mu.g (i.p. daily for 10 days) of either purified monoclonal anti-GM-CSF IgG or isotype control. Daily mean clinical scores (.+-.SEM) are presented.

FIG. 3A is a graphical representation showing that anti-GM-CSF therapy prevents COPD-like inflammation in mice. Levels of neutrophils recovered in lung lavage fluid (BAL) reflect the intensity of inflammation induced by the bacterial wall component, lipopolysaccharide (LPS) (10 .mu.g administered transnasally). Anti-GM-CSF (22E9) therapy dose-dependently suppressed the inflammatory response when administered 3 hrs prior to LPS. Note that very high dose glucocorticoid steroid therapy (dexamethasone) produced only slight suppression. Data are expressed as means.+-.SEM for n=10-20 mice/data point. The actual amounts of Ab used were {fraction (1/100)} the quantities shown.

FIG. 5 is a graphical representation showing that anti-GM-CSF inhibits lipopolysaccharide (LPS)-induced exacerbation of asthma. Balb/c mice were sensitized to ovalbumin and challenged over 3 days by aerosol of qualbumin to elicit eosinophilic lung inflammation. Neutrophilic inflammation was elicited by instilling 100 ng/ml LPS into the lungs and measuring responses 24 hrs later. Data are shown as mean lung lavage cell counts/ml fluid.+−.SEM for n=8-10 mice/group.

DETAILED DESCRIPTION OF THE PREFERRED EMBODIMENTS

The present invention is predicated in part on a two tier strategy for controlling inflammation in a subject. At one level, it is proposed to reduce macrophage proliferation, activation, growth and/or survival. At a second level, it is proposed to reduce the level of production of pro-inflammatory mediators such as but not limited to IL-1, TNF-.alpha. and/or the neutral proteinase, u-PA. The latter level in the strategy is particularly amenable to local therapeutic intervention, i.e. at the site of inflammation. The two tier strategy may be adopted separately or in combination.

Accordingly, one aspect of the present invention contemplates a method for ameliorating the effects of inflammation in a subject, said method comprising administering an agent which inhibits or otherwise antagonizes the effects of a colony stimulating factor on cells of the monocyte/macrophage lineage thereby reducing the level of proliferation, activation, growth and/or survival of said cells.

In a particularly preferred aspect, the present invention provides a method for ameliorating the effects of inflammation in a subject, said method comprising administering an agent which inhibits or otherwise antagonizes the effects of two or more colony stimulating factors on cells of the monocyte/macrophage lineage thereby reducing the level of cell proliferation, activation, growth and/or survival of said cells.

In a related embodiment, the present invention provides a method for ameliorating the effects of inflammation in a subject, said method comprising administering an agent which inhibits or otherwise antagonizes the activity of u-PA and optionally other inflammatory mediators produced by a cell of the monocyte/macrophage lineage.

The preferred cells of the monocyte/macrophage lineage are macrophages. However, the present invention extends to any other related cells which are activated, proliferate, growth and/or survival in response to colony stimulating factors and/or which mediate an effect via inflammatory mediators (e.g. u-PA).

The term "inflammatory condition" is used in its broadest sense but preferably relates to chronic inflammation conditions such as rheumatoid arthritis, inflammatory bowel disease, Crohns disease, type I diabetes, multiple sclerosis, psoriasis and chronic inflammatory lung disease such as asthma, chronic bronchitis, emphysema or chronic obstructive airway disease. Generally, but not exclusively, the inflammatory condition is localized. Frequently, inflammation involves pro-inflammatory mediators such as TNF-.alpha. and IL-1 amongst others including u-PA.

The term "ameliorate" is used here in its broadest sense to refer to the reduction of the symptoms exhibited in patients suffering from an inflammatory condition. It also covers the more specific response of reducing the levels of inflammatory and pro-inflammatory mediators such as macrophage colony-stimulating factor (M-CSF), granulocyte, macrophage colony-stimulating factor (GM-CSF), IL-1, TNF-.alpha., Interleukin 6 (IL-6), products of COX-2, u-PA amongst other molecules. The term "ameliorate" also covers a method of treating a subject exhibiting inflammation.

In a preferred embodiment, at least two colony-stimulating factors are targeted for antagonism. Most preferably, the two colony-stimulating factors are M-CSF and GM-CSF or related molecules. A related molecule is one which at the functional, physiological, immunological or structural level is similar to M-CSF or GM-CSF.

Accordingly, another aspect of the present invention contemplates a method for ameliorating the effects of inflammation in a subject, said method comprising administering an agent which inhibits or otherwise antagonizes the effects on M-CSF and/or GM-CSF on cells of the monocyte/macrophage lineage thereby reducing the level of cell proliferation, activation, growth and/or survival.

The term "agent" is used in its broadest sense to include a composition comprising a single valent molecule capable of inhibiting a colony-stimulating factor such as M-CSF or GM-CSF or a multivalent molecule capable of inhibiting two or more colony stimulating factors or two or more molecules which separately or in combination inhibit two or more colony-stimulating factors. The molecules making up an agent include soluble colony-stimulating factor receptors, binding proteins to a colony-stimulating factor, immunointeractive molecules (e.g. antibodies) capable of interacting with a colony-stimulating factor or its receptor and molecules such as those found through natural product screening which act as antagonists of colony-stimulating factor-receptor interaction. When the antagonizing molecules are antibodies, these may be produced in the same species as the subject being treated or they may be made in another species but rendered immunologically similar to a homologue from the species being treated. For example, when the subject is a human, a mouse anti-human antibody to M-CSF or GM-CSF may be employed in humans once the antibody has been humanized.

Natural product screening includes the screening of environments such as plants, coral, sea and river beds and microorganisms for molecules and generally small molecules, which are capable of acting as antagonists of colony-stimulating factor-receptor interaction. Alternatively, chemical libraries may be screened for synthetic chemicals which act in a similar manner. In yet a further alternative, the receptor for the colony-stimulating factor such as the M-CSF and GM-CSF receptors are produced in soluble form. This acts as an antagonist by competing for the receptor on the monocyte/macrophage lineage cells for the colony-stimulating factors.

Another useful form of the agent exploits the biology of monocyte/macrophage surface proteins and internalization mechanisms. In this regard, the preferred agents do not activate the monocyte/macrophages but are internalized by the monocyte/macrophage cells. In one embodiment, an agent comprises a monocyte/macrophage-interacting ligand chemically linked to an active portion such as but not limited to a drug, antibody or pro-drug. A "drug" includes a nucleic acid molecule such as a sense, antisense or ribozyme molecule. A "pro-drug" is a molecule which, upon activation such as chemical activation, becomes active.

Conveniently, but not necessarily, the chemical linkage is in the form of an enzyme sensitive bond. Furthermore, the agent may be encapsulated in a material which permits exposure of the monocyte/macrophage interacting ligand. For example, the agent is formulated in a lipid bilayer or equivalent including an artificial membrane. In an alternative embodiment, the agent is not encapsulated and is administered directly.

Presentation of the formulation to a monocyte/macrophage permits internalization and, generally, dissociation of the ligand from the active portion. The active portion may be any of a number of molecules such as those which reduce expression of colony-stimulating factor receptor formation, which antagonizes the signal induced by a colony-stimulating factor and/or which antagonize the production of one or more inflammatory mediators such as but not limited to u-PA.

Conveniently, the monocyte-macrophage interacting ligands are sugars.

Accordingly, another aspect of the present invention contemplates a method for ameliorating the effects of inflammation in a subject, said method comprising administering to said subject an effective amount of an agent comprising a monocyte/macrophage interacting ligand chemically linked to an active portion and wherein said agent is in an encapsulated form such that the monocyte/macrophage interacting portion is represented on the outer surface of said encapsulation while the active portion is part of the encapsulated wall or is internal relative to the encapsulation wall such that a monocyte/macrophage cell is capable of internalizing said encapsulated agent and wherein said active portion of said agent antagonizes colony-stimulating factor mediation, proliferation, activation, growth and/or survival of said monocyte/macrophage and/or antagonizes the production or activity of one or more inflammatory mediators.

Particularly preferred colony-stimulation factors include M-CSF and/or GM-CSF.

Particularly preferred inflammatory mediators include u-PA.

In yet another embodiment, the agent is provided in a non-encapsulated form.

According to this embodiment, there is provided a method for ameliorating the effects of inflammation in a subject, said method comprising administering to said subject an effective amount of an agent comprising a monocyte/macrophage interacting ligand chemically linked to an active portion or a pro-active form thereof and wherein said active portion of said agent antagonizes colony-stimulating factor mediated proliferation, activation, growth and/or survival of said monocyte/macrophage cell and/or antagonizes the production or activity of one or more inflammatory mediators from said monocyte/macrophage cells.

The present invention further contemplates the agents useful in the practice of the instant method.

Accordingly, in one embodiment, the present invention is directed to an agent comprising a monocyte/macrophage interacting ligand chemically linked to an active portion and wherein said agent is in an encapsulated form such that the monocyte/macrophage interacting portion is represented on the outer surface of said encapsulation while the active portion is part of the encapsulated wall or is internal relative to the encapsulation wall such that a monocyte/macrophage cell is capable of internalizing said encapsulated agent and wherein said active portion of said agent antagonizes colony-stimulating factor mediation, proliferation, activation, growth and/or survival of said monocyte/macrophage and/or antagonizes the production or activity of one or more inflammatory mediators.

In another embodiment, the agent comprises administering to said subject an effective amount of an agent comprising a monocyte/macrophage interacting ligand chemically linked to an active portion or a pro-active form thereof and wherein said active portion of said agent antagonizes colony-stimulating factor mediated proliferation, activation, growth and/or survival of said monocyte/macrophage cell and/or antago-nizes the production or activity of one or more inflammatory mediators from said monocyte/macrophage cells.

Alternative agents which target colony-stimulating factors and/or inflammatory mediators include agents capable of stimulating a local or systemic immune response to a colony-stimulating factor and/or an inflammatory medication and small molecules based on pharmacore drug template models of colony-stimulator factors, their receptors and/or inflammatory mediators such as u-PA.

The subject is preferably a human but the instant invention extends to primates, livestock animals, laboratory test animals, companion animals and captured wild animals.

With respect to blocking u-PA activity, again, this may be accomplished using anti-u-PA antibodies, antagonists located in natural product screening or screening of chemical libraries, as discussed above. Furthermore, in a particularly preferred embodiment, the u-PA antagonist treatment may applied locally to the site of inflammation such that the antagonizing effects are maintained at the site of inflammation. A similar approach may be adopted for other inflammatory mediators.

Either treatment strategy may be adopted or both strategies may be adopted in tandem.

According to the latter embodiment, the present invention provides a method for ameliorating the effects of inflammation in a subject, said method comprising administering one or more agents to antagonize the effects of a colony-stimulating factor on cells of the monocyte/macrophage lineage thereby reducing cell proliferation, activation, growth and/or survival and which antagonize the effects of u-PA and optionally other inflammatory mediators produced by said cells of monocyte/macrophage lineage.

A single valent or single multivalent agent may be employed or multiple agents may be used each containing antagonists for the colony-stimulating factors and/or the inflammatory mediators such as u-PA.

Preferably, the colony-stimulating factors are M-CSF and GM-CSF.

Preferably, the cells of monocyte/macrophage lineage are macrophages.

Other agents useful in the practice of the present invention include mimotopes or their chemical or biological equivalents. Antibodies are produced in response to B cell-recognized epitopes present on macromolecular biological molecules. The epitope can be a linear sequence of amino acids or a discontinuous epitope of chemical groups spatially arranged, i.e. a conformational epitope. The recognition and binding site of an antibody can be mapped using small peptides. The resultant peptide is referred to herein as a mimotope. This may be made from all L amino acids or a mixture of D and L amino acids. Amino acids not found in human proteins can also be used to make mimotope. The mimotope mimics the epitopes generating the antibody. This is useful as a drug design template or as an antigen to produce a monoclonal antibody to an epitope that is difficult to characterize. Mimotopes recognized by anti-GM-CSF and anti-M-CSF monoclonal antibodies are encompassed by the present invention. Furthermore, a drug design template is also encompassed by the present invention. In this template, cyclic peptides are made and screened in bioassays to determine the minimal structure and constraints. Based on this information, a template is designed which, after modification, leads to low molecular weight blockers. Such blockers are useful as therapeutic agents. The present invention further contemplates a variety of mimetics such as mimetics of the mimotopes.

The agents of the present invention are preferably in a form suitable for pharmaceutical use.

Agents useful in modulating the effects of colony-stimulating factors in mediated monocyte/macrophage proliferation, activation, growth and/or survival can be usefully screened and assessed using a range of animal models including animals having reduced levels of one or more colony-stimulating factors through either genetic manipulation and/or antibody or colony-stimulating factor antagonist therapy.

The present invention is directed to a number of animal models useful in assessing the efficacy of agents useful in the treatment of inflammation. In one model, an asthma-like inflammation of the airways is elicited in mice or other suitable animal by administration of ovalbumin proteins absorbed to an adjuvant. The ovalbumin may be administered to the animal by any suitable means such as by injection (e.g. i.p. injection) or via nasal administration (e.g. via aerosol. This stimulates an immune response and causes an eosinophilic inflammation of the lung reminiscent of asthma. The model has predictive value for drugs active against asthma and also allergic drugs active against the underlying "TH2 immune deviation" elicited by immunization.

In another model, the COPD model, a COPD-like neutrophil-rich macrophage-activation dependent inflammation is elicited in animals such as mice by transnasal instillation of the bacterial cell wall component lipopolysaccharide (LPS) with or without prior manipulation or treatment of the animal. The ongoing inflammatory response involves the cytokines TNF-.alpha. and chemokines. A characteristic of this inflammatory response is its resistance to the anti-inflammatory effects of glucocorticosteroids. Animals responded with marked-dose dependent neutrophilic inflammation, release of inflammatory cytokines and macrophage-activation. The model has predictive value for human COPD, bronchitis and emphysema.

Yet another model, the exacerbation model, an animal model is employed wherein an asthma response is elicited in a manner similar to the asthma model using three challenges in three consecutive doses. Lipopolysaccharide is also instilled into the lungs of mice to elicit a neutrophilic/macrophage inflammatory response with an underlying eosinophilic inflammation. The model has predictive value for identifying treatments of exacerbation of human asthma.

Still a further model employs the administration of methylated BSA followed by the subcutaneous administration of a cytokine such as GM-CSF and/or M-CSF. Such animals develop a condition similar to arthritis and are useful for screening for anti-inflammatory drugs (e.g. anti-GM-CSF and/or anti-M-CSF agents).

All these models are encompassed and covered by the present invention as are agents identified for the treatment and inflammation using such models. Furthermore, the present invention contemplates in vitro models. One such model employs cell-based and biochemical assays as part of a drug screening protocol. Monocyte/macrophage populations are the preferred cell-based assays. Preferred biochemical assays include protease, kinase and cytokine assays. Such assays screen for agents which modulate monocyte/macrophage protease, kinase or cytokine function or which modulate the activity of pro-inflammatory effector molecules.

Preferably, the animal models are mice or other rodents and most preferably are inbred mice, outbred mice or genetically altered mice or cross-hybrids thereof. The preferred strains are Balb/c, C57/B16, c129 and congenic or genetically modified derivatives of these strains, beige mice and mice genetically susceptible to asthma-like or COPD-like asthma responses.

Another aspect of the present invention is directed to a composition comprising one or more molecules capable of antagonizing the ability of a colony-stimulating factor from activating, proliferating, inducing growth and/or survival of cells of a monocyte/macrophage lineage, said composition further comprising one or more pharmaceutically acceptable carriers and/or diluents.

The composition may comprise two antagonists, one for each colony-stimulating factor. Alternatively, a single, multivalent antagonist is employed capable of antagonizing two or more colony-stimulating factors. Yet a further alternative provides a composition in a two part format with a single valent agent in each composition.

In a particularly preferred embodiment, the colony-stimulating factors are M-CSF and GM-CSF. Preferably, the antagonists are immunointeractive molecules such as antibodies.

Accordingly, the present invention provides a composition comprising two immunointeractive molecules wherein one is specific for M-CSF and another is specific for GM-CSF, said composition further comprising one or more pharmaceutically acceptable carriers and/or diluents wherein said composition is useful in the treatment of inflammation.

Yet another embodiment of the present invention is directed to a composition comprising an antagonist of u-PA and optionally an antagonist of one or more other inflammatory mediators produced by cells for monocyte/macrophage lineage and one or more pharmaceutically acceptable carriers and/or diluents.

Still yet another embodiment of the present invention provides a composition comprising immunointeractive molecules to M-CSF and GM-CSF and an antagonist of u-PA and optionally one or more antagonists to one or more other inflammatory mediators produced by cells of a monocyte/macrophage lineage and one or more pharmaceutically acceptable carriers and/or diluents.

For convenience, the terms "agent", "composition" and "pharmaceutical composition" are used herein interchangeably.

Administration of the agent, such as in the form of a pharmaceutical composition, may be performed by any convenient means. The agent is contemplated to exhibit therapeutic activity when administered in an amount which depends on the particular case. The variation depends, for example, on the human or animal and the agent chosen. A broad range of doses may be applicable. Considering a patient, for example, from about 0.1 .mu.g to about 1 mg of agent may be administered per dosing, and more preferably 0.1 .mu.g to about 50 .mu.g per dosing. Dosage regimes may be adjusted to provide the optimum therapeutic response. For example, doses may be administered daily, weekly, monthly or other suitable time intervals or the dose may be proportionally reduced as indicated by the exigencies of the situation. The agent may be administered in a convenient manner such as by the oral, intravenous (where water soluble), intranasal, intraperitoneal, intramuscular, intracranial, intraocular, intrathecal, intracerebrally, infusion, subcutaneous, intradermal or suppository routes or implanting (e.g. using slow release molecules) as well as via direct lung delivery. They may also be administered rectally or using a vapour or aerosol.

Compositions suitable for injectable use include sterile aqueous solutions (where water soluble) and/or emulsions or liposome preparations or sterile powders for the extemporaneous preparation of sterile injectable solutions. They must be stable under the conditions of manufacture and storage and must be preserved against the contaminating action of microorganisms such as bacteria and fungi. The carrier can be a solvent or dispersion medium containing, for example, water, ethanol, polyol (for example, gylcerol, propylene glycol and liquid polyethylene glycol, and the like), suitable mixtures thereof and vegetable oils. The preventions of the action of micro-organisms can be brought about by various antibacterial and antifungal agents, for example, parabens, chlorobutanol, phenol, sorbic acid, thirmersal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin or encapsulation in a biocompatible polymer such as PLA polylactic and/or PLG polyglycolic acid.

Sterile injectable solutions are prepared by incorporating the active compounds in the required amount in the appropriate solvent with various of the other ingredients enumerated above, as required, followed by sterilization. Dispersions are also contemplated and these may be prepared by incorporating the various sterilized active ingredients into a sterile vehicle which contains the basic dispersion medium and the required other ingredients from those enumerated above. In the case of sterile powders for the preparation of sterile injectable solutions, a preferred method of preparation includes vacuum drying and the freeze-drying technique which yield a powder of the active ingredient plus any additional desired ingredient from a previously sterile-filtered solution.

When the active ingredients are suitably protected they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 5 to about 80% of the weight of the unit. The amount of active compound in such therapeutically useful compositions is such that a suitable dosage 5 will be obtained. Preferred compositions or preparations according to the present invention are prepared so that an oral dosage unit form contains between about 0.1 .mu.g and 2000 mg of active compound.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Any material used in preparing any dosage unit form should be pharmaceutically pure and substantially non-toxic in the amounts employed. In addition, the active compound may be incorporated into sustained-release preparations and formulations.

The present invention also extends to forms suitable for topical applications such as creams, lotions and gels. This is particularly advantageous for the treatment of local inflammation. Furthermore, forms suitable for inhalable administration such as aerosols, powders and instillations are encompassed by the present invention. The term inhalable administration includes direct lung delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material.

Effective amounts of the composition contemplated by the present invention will vary depending on the severity of the pain and health and age of the recipient. In general, effective amounts may vary from 0.01 ng/kg/body weight to about 1 mg/kg/body weight and preferably 0.01 ng/kg body weight to about 1 .mu.g/kg body weight. Alternative amounts range from 0.1 ng/kg/body weight is about 10 .mu.g/kg/body weight or from 1.0 ng/kg body weight to about 80 .mu.g/kg body weight.

The pharmaceutical composition may also comprise genetic molecules such as a vector capable of transfecting target cells where the vector carries a nucleic acid molecule or derivative or analogue thereof capable of expressing a cytokine or cytokine receptor. The vector may, for example, be a viral vector.

The agent may also be linked to a targeting means such as monoclonal antibody, which provides specific delivery of the agent to a target region.

In accordance with a method of the invention, the immunogenic agent may be co-administered with one or more other compounds or molecules. For example, the agent may be co-administered with another molecule designed to reduce or alleviate any one or more symptoms of an inflammatory response. By "co-administered" is meant simultaneous administration in the same formulation or in two different formulations via the same or different routs or sequential administration by the same or different routes. By "sequential administration" is meant a time difference of from seconds, minutes, hours or days between the administration of the two types of molecules. These molecules may be administered in any order.

As stated above, the present invention extends to the use of genetic means to reduce colony-stimulating factor-induced activation and proliferation of cells of macrophage lineage. For example, a genetic construct comprising a sequence of nucleotides which, for example, act as antisense molecules to colony-stimulating factor receptor gene-specified mRNA. Alternatively, the nucleotide sequence defines a ribozyme specific for the target mRNA. Yet another alternative provide the colony-stimulating factor receptor gene in sense orientation to induce co-suppression. A similar approach may be used to down-regulate u-PA. The genetic construct may be administered as part of a viral vector or may be administered as a naked nucleic acid molecule. Administration is conveniently but not exclusively via injection.

The present invention further contemplates, in a preferred embodiment, the use of a M-CSF antagonist and a GM-CSF antagonist in the manufacture of a medicament for the treatment of inflammation in a subject.

In an alternative embodiment, the present invention provides for the use of a u-PA antagonist and/or an antagonist of one or more other pro-inflammatory mediators for the manufacture of a medicament for the treatment of inflammation in a subject.

In yet a further embodiment, the present invention is directed to the use of a M-CSF antagonist, a GM-CSF antagonist and a u-PA antagonist and/or antagonist of one or more other pro-inflammatory mediators in the manufacture of a medicament for the treatment of inflammation in a subject.

The term "antagonist" is intended to be considered in its broadest sense to include molecules which inhibit the activity of the colony-stimulating factor such as M-CSF and GM-CSF or the activity of u-PA or other inflammatory mediators. The term also includes genetic molecules which are useful in down-regulating expression or translation of genes encoding the receptors for the colony-stimulating factors or reducing levels of u-PA.

As stated above, the composition may also be in the form of an encapsulated or non-encapsulated agent.

The present invention further extends to the specific targeting of GM-CSF in the treatment of neutrophil-mediated inflammatory. It is proposed that GM-CSF promotes neutrophil survival and activation. Accordingly, anti-GM-CSF therapy is proposed to be useful in the treatment of neutrophil-mediated inflammation (see FIG. 3A).

The present invention is further described by the following non-limiting Examples.

Example 1

Therapeutic Concept

Figure 1:
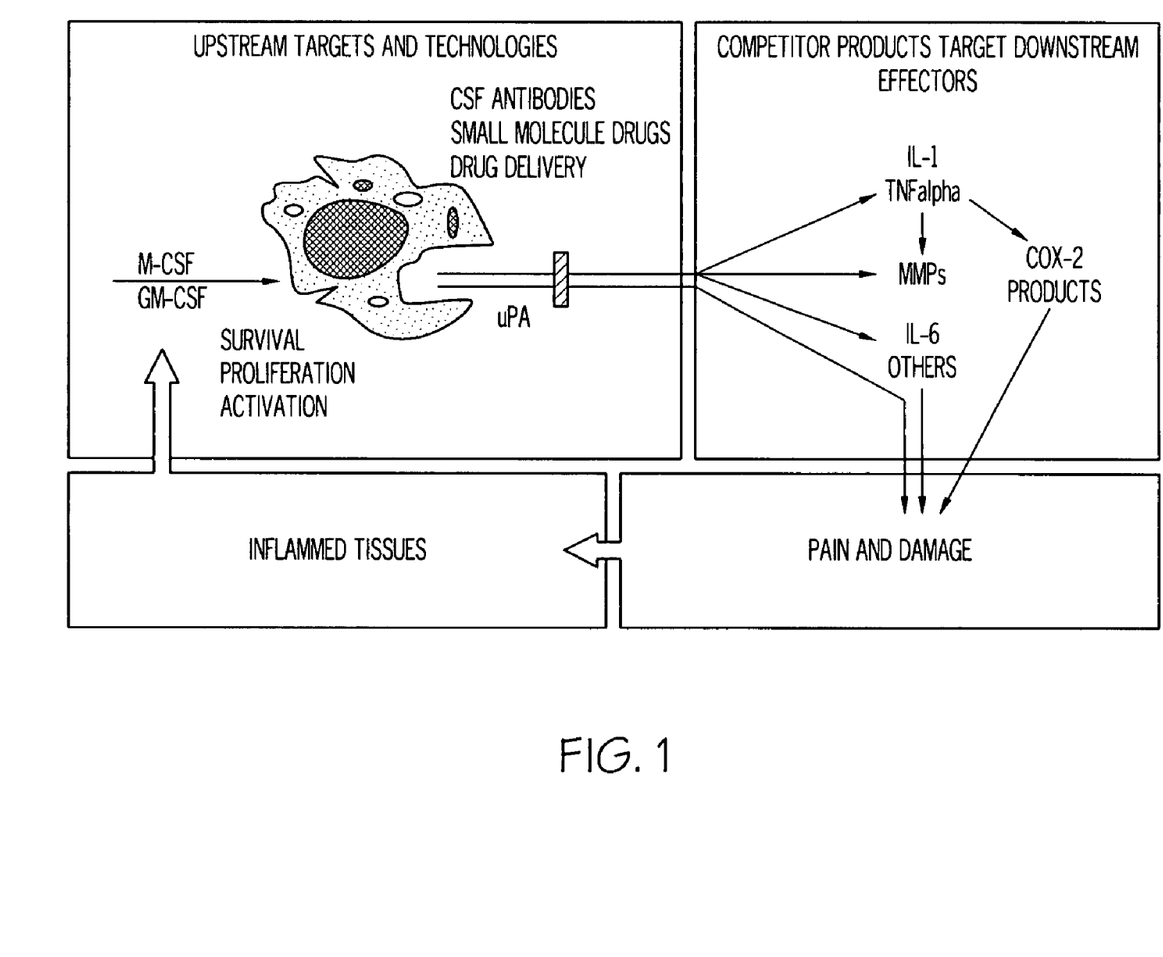

The therapeutic concept upon which the present invention is based is shown FIG. 1 In essence, targeting colony-stimulating factors such as M-CSF and GM-CSF results in fewer and/or less active monocytes/macrophages available to produce inflammatory cytokines and other mediators such as u-PA.

Example 2

M-CSF and GM-CSF in Inflammatory Diseases

Figure 2A:
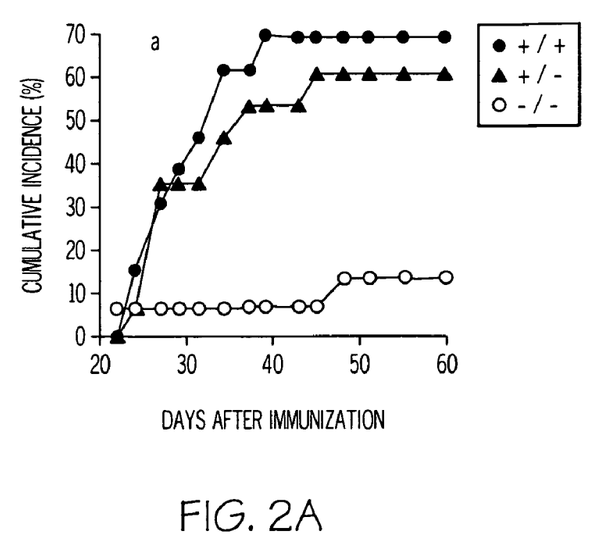
FIG. 2A is a graphical representation showing collagen-induced arthritis (CIA) development in GM-CSF-deficient mice and littermate controls. The incidence of arthritis (shown as cumulative %) of GM-CSF-/- (n=15), GM-CSF+/- (n=28) and GM-CSF+/+ (n=13) mice is shown with time following primary immunization with CII. The final incidence of arthritis was significantly lower in the GM-CSF-/- mice compared to the GM-CSF+/+ and GM-CSF+/- mice (p<0.005 for each, $X^2$ test). The terms "-/+", "+/-" and "+/+" relate to homozygous or heterozygous absence (-) or present (+) of a particular gene or allele.

Murine arthritis models and murine lung models are used to test the concept outlined in Example 1. From the arthritis models, it has been found that M-CSF and GM-CSF exacerbate disease. From both gene knockout and antibody blocking data, direct evidence has now been obtained by the inventors for their involvement in disease progression. In FIG. 2, it can be seen that GM-CSF-/- mice develop minor collagen-induced arthritis (CIA) disease in the occasional digit. Surprisingly, it was found that the humoral response (four isotypes) to collagen type II (CII) was not compromised. The results are shown in FIG. 2A.

Figure 2B:
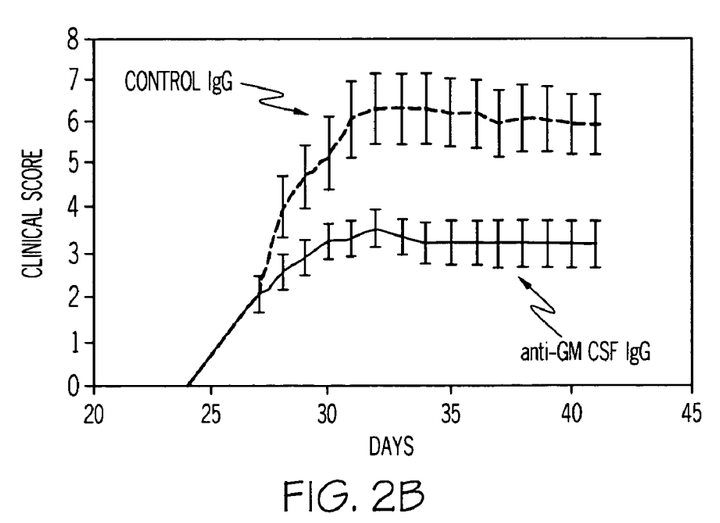
Figure 2C:
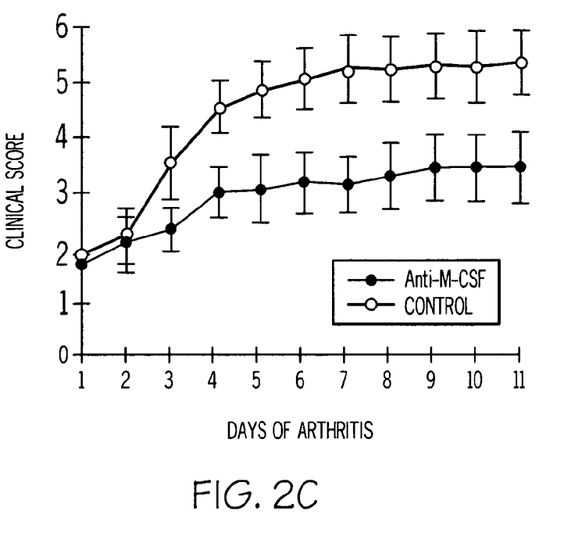
FIG. 2C is a graphical representation showing the effect of anti-M-CSF antibody on CIA development. Same protocol as for FIG. 1B except that mice were given either purified monoclonal anti-M-CSF IgG or isotype control.

A monoclonal antibody to GM-CSF prevents the onset of arthritis and suppresses established disease (FIG. 2B). The anti-GM-CSF mAb blocking in the CIA model provides more efficacy than the alleviation achieved by anti-TNF-.alpha. therapy in the same model. Similar results are observed using anti-M-CSF mAb blocking antibody (FIG. 2C).

Example 3

M-CSF and GM-CSF in Inflammatory Lung Disease

Figure 3A:
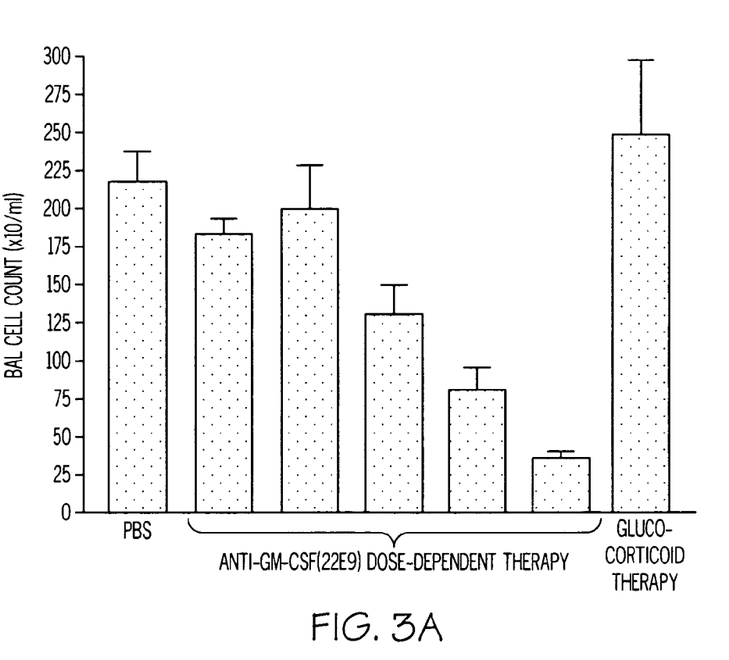
Figure 3B:
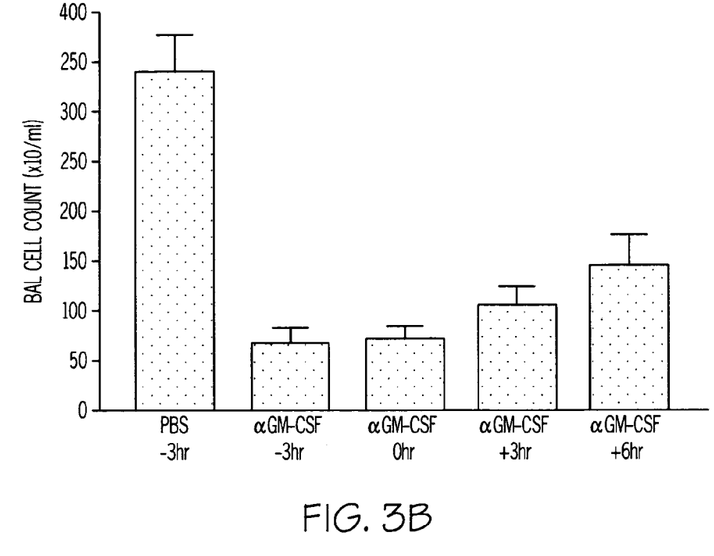
FIG. 3B is a graphical representation showing the anti-GM-CSF-therapy reverses COPD-like inflammation in the lung. Anti-GM-CSF therapy (300 .mu.g/mouse) prevented LPS-induced neutrophilia even when added 3-6 hrs after the stimulus. Data are expressed as means.+-.SEM for n=10-20 mice.
Figure 3C:
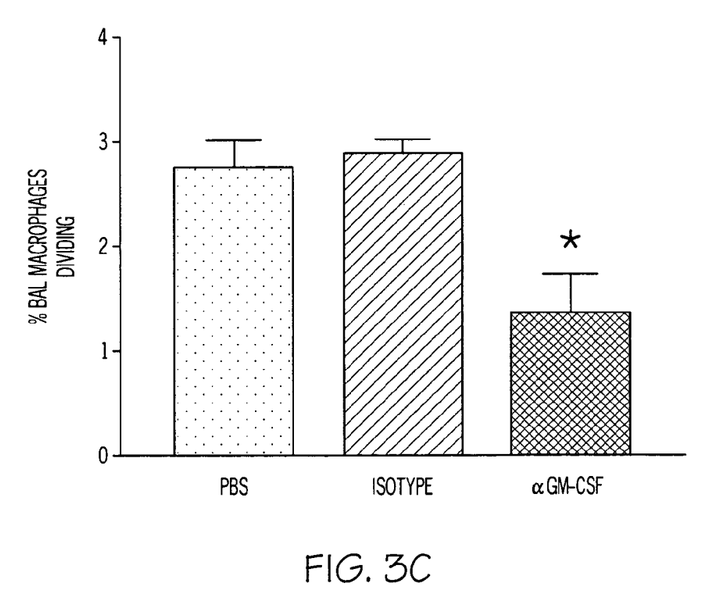
FIG. 3C is a graphical representation showing the suppression of macrophage replication by anti-GM-CSF therapy in experimental COPD in mice. Macrophage replication is quantified by the number of mitotic figures observed histologically. Data are expressed as means.+-.SEM for n=10-20 mice.
Figure 3D:
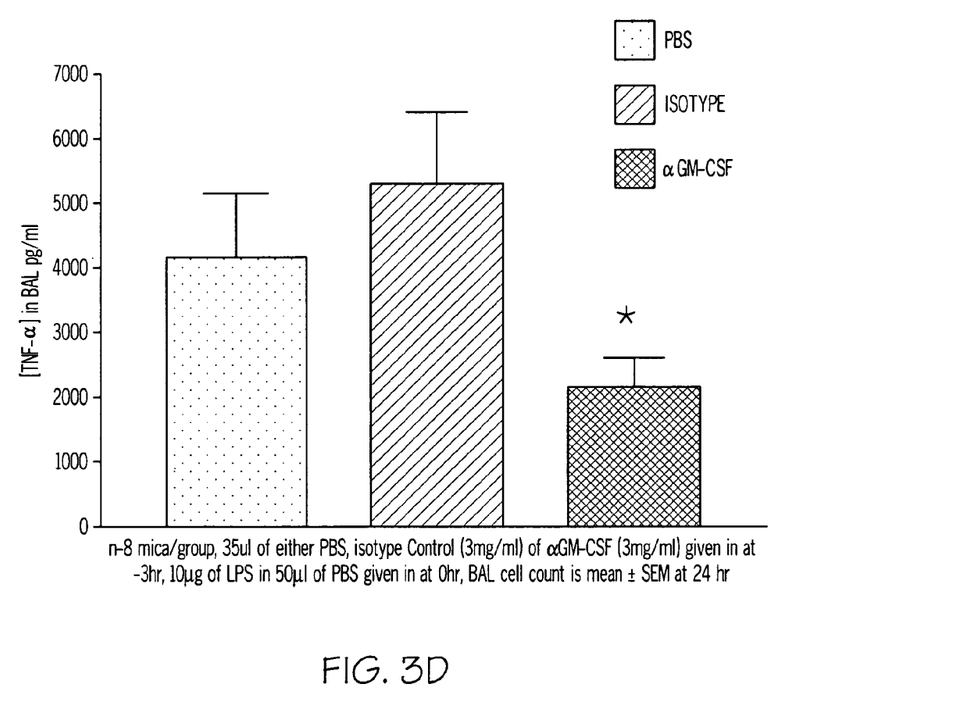
FIG. 3D is a graphical representation showing suppression of TNF-.alpha. formation by anti-GM-CSF therapy of experimental COPD in mice. Anti-GM-CSF therapy suppressed TNF-.alpha. levels in BAL of mice given LPS (10 .mu.g transnasally administered). The antibody was given 3 hrs prior to LPS administration and TNF-.alpha. levels determined by ELISA 6 hrs later. Data are mean values.+-.SEM (n=10 mice).

In both a murine COPD model, as well as in a murine allergic (asthma) inflammation model, blocking mAbs to both CSFs suppresses disease. FIG. 3A shows that blocking antibody to GM-CSF can prevent endotoxin-induced lung neutrophilia (a COPD model) even when added after the stimulus (FIG. 3B). This provides support for the use of anti-GM-CSF therapy in the treatment of neutrophil-mediated inflammation in addition to macrophage-mediated inflammation and/or tissue damage transformation. FIG. 3C demonstrates that this antibody suppresses local macrophage proliferation in the same model. FIG. 3D demonstrates the suppression of TNF-a formation by anti-GM-CSF therapy. The favourable effect of anti-GM-CSF therapy compared to that found with a glucocorticoid is worth noting (FIG. 3A). The latter class of drugs have potent anti-inflammatory activity but COPD patients are notably refractory to them. The data in FIG. 3A are consistent with this weak clinical efficacy; the data are also consistent with the observation that glucocorticoids do not inhibit the production of GM-CSF by ex vivo lung tissue.

Example 4 u-PA/Plasmin in Inflammatory Disease

Figure 4:
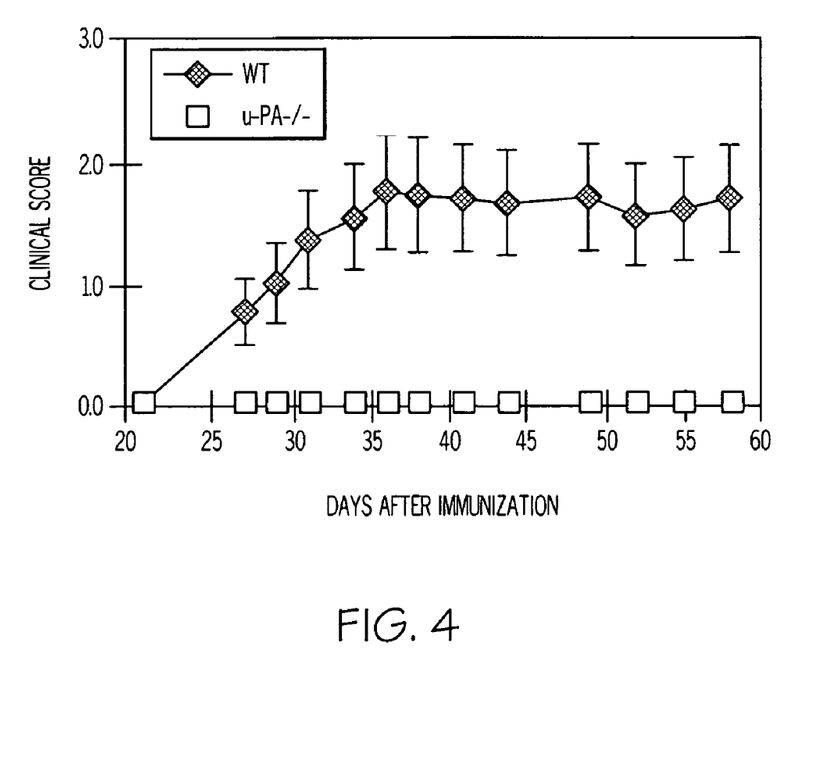
FIG. 4 is a graphical representation showing collagen-induced arthritis (CIA) development in u-PA-/- deficient mice and wild-type controls. The severity of arthritis, expressed as a clinical score of u-PA-/- (n=50) and wild-type control (n=50) mice is shown with time following primary immunization with CII. There was no detectable disease in the u-PA-/- mice.
Figure 5:
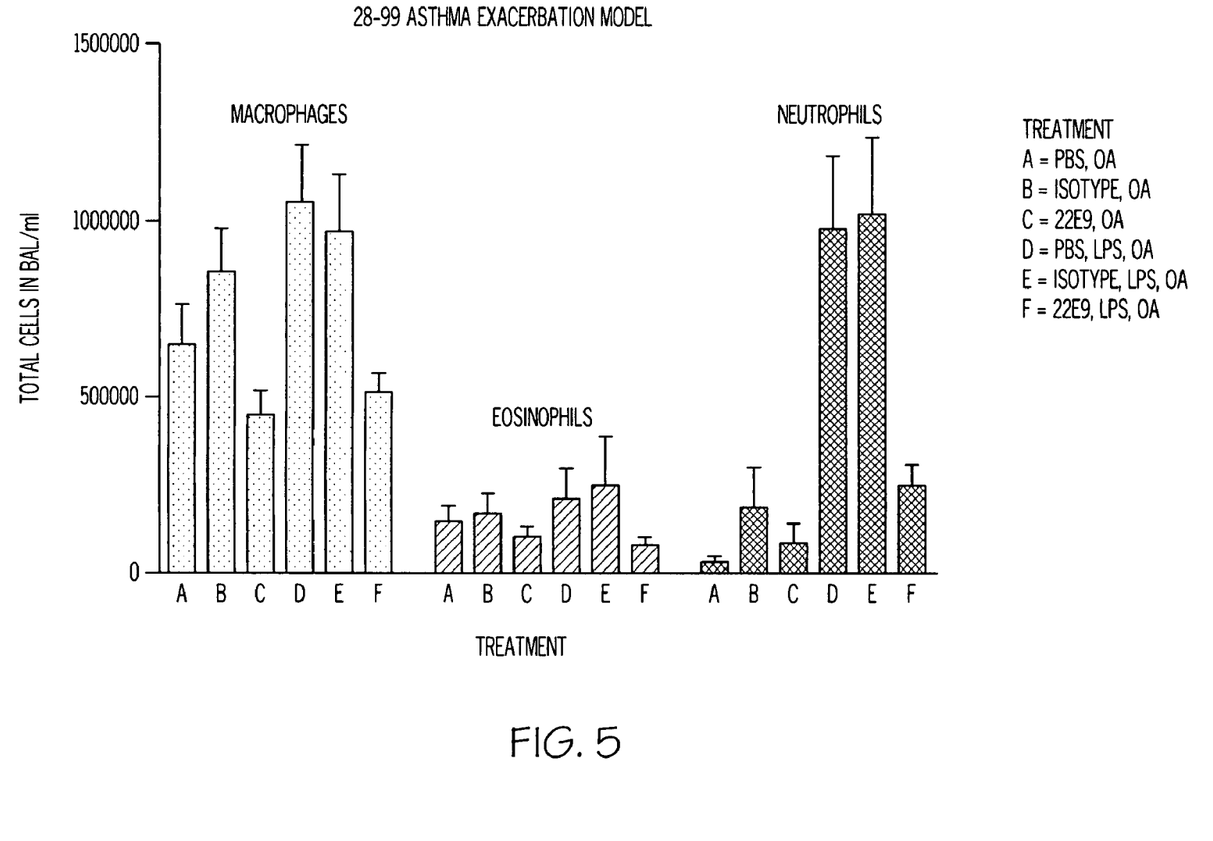

The inventors developed u-PA-/- mice. FIG. 4 supports the concept that u-PA is one way in which M-CSF and GM-CSF behave as pro-inflammatory cytokines. u-PA-/- mice do not develop CIA (FIG. 4). These data are similar to what has been found for this model in GM-CSF-/- (FIG. 2A) and M-CSF-/- mice.

Example 5

Animal Models

1. Asthma

Asthma-like inflammation of the airways is elicited in mice by i.p. injection of ovalbumin protein (grade V, 10 .mu.g/animal) absorbed to the adjuvant Al(OH).sub.3 on day 0 and day 14. Commencing on day 21, animals receive a challenge with ovalbumin solution delivered either transnasally (50 .mu.l volume) while under anaesthetic or by aerosol while conscious. This restimulates the immune system and causes an eosinophilic inflammation of the lung reminiscent of asthma. If the challenge is repeated, e.g. once daily for three days or intermittently over weeks, pathophysiological features of asthma observed in the acute models can be elicited more strongly, e.g. bronchial hyper-reactivity, mucus induction and airway wall remodelling. The model has predictive value for drugs active against asthma and also anti-allergic drugs active against the underlying TH2 immune deviations elicited by the immunization and for identifying mechanisms of disease. Key cytokines known to affect the system include but are not limited to IL-4, IL-5, TNF-.alpha., IFN-.gamma., IL-12, IL-13, IL-19, IL-10 and IL-1.

2. COPD

A COPD-like neutrophil-rich and macrophage activation-dependent inflammation is elicited in mice by instillation, under anaesthetic, of the bacterial cell well component, lipopolysaccharide (LPS) dose, usually 1 pg-100 ng/mouse. The ongoing acute inflammatory response involves the cytokines TNF-.alpha. and chemokines. A characteristic of this inflammatory response is its resistance to the anti-inflammatory effects of glucocorticosteroids. Animals respond with marked dose-dependent neutrophilic inflammation, release of inflammatory cytokines and macrophage activation. After several days, macrophages typically proliferate, a feature also seen in human COPD. The model has predictive value for identifying mechanisms and treatments of human COPD, bronchitis and emphysema.

3. Novel Exacerbation Model

Sudden neutrophilic inflammation of the airways occurs in most exacerbations of asthma. The inventors have developed a new model where an asthma response is elicited as described in (1) above using three challenges on three consecutive days. On day 24, LPS is instilled into the lungs of mice, usually at 10 ng/mouse, to elicit a neutrophilic/macrophage inflammatory response on top of the underlying eosinophilic inflammation. The model has predictive value for identifying mechanisms and treatments of exacerbation of human asthma.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A method for ameliorating the effects of inflammatory disease in a subject, comprising administering to the subject an antagonist of uPA.

2. The method of claim 1, wherein said antagonist comprises an antibody that specifically binds uPA.

3. The method of claim 1, wherein said subject is human.

4. The method of claim 1, wherein said inflammatory disease is selected from the group consisting of rheumatoid arthritis, inflammatory bowel disease, Crohns disease, type I diabetes, multiple sclerosis, psoriasis and chronic obstructive lung disease.

5. The method of claim 4, wherein said chronic obstructive lung disease is selected from the group consisting of asthma, chronic bronchitis, emphysema, and chronic obstructive airway disease.

6. The method of claim 1, wherein the method of administration comprises intravenous, subcutaneous or local administration.

7. The method of claim 1, further comprising administration of an antagonist of a colony stimulating factor, wherein the colony stimulating factor is selected from the group consisting of GM-CSF and M-CSF.

* * * * *